US012383753B2

(12) United States Patent
Yan et al.

(10) Patent No.: US 12,383,753 B2
(45) Date of Patent: Aug. 12, 2025

(54) METHOD AND SYSTEM OF SENSITIZING CANCER CELLS TO CHEMICAL TREATMENT BY PLASMA BASED ACTIVATION

(71) Applicant: The George Washington University, Washington, DC (US)

(72) Inventors: Dayun Yan, Ashburn, VA (US); Michael Keidar, Baltimore, MD (US); Eda Gjika, Washington, DC (US)

(73) Assignee: George Washington University, Washington, DC (US)

( * ) Notice: Subject to any disclaimer, the term of this patent is extended or adjusted under 35 U.S.C. 154(b) by 1111 days.

(21) Appl. No.: 15/734,149

(22) PCT Filed: May 31, 2019

(86) PCT No.: PCT/US2019/034999
§ 371 (c)(1),
(2) Date: Dec. 1, 2020

(87) PCT Pub. No.: WO2019/232438
PCT Pub. Date: Dec. 5, 2019

(65) Prior Publication Data
US 2021/0213297 A1    Jul. 15, 2021

Related U.S. Application Data

(60) Provisional application No. 62/679,174, filed on Jun. 1, 2018.

(51) Int. Cl.
*A61N 1/44* (2006.01)
*A61K 31/4188* (2006.01)
(Continued)

(52) U.S. Cl.
CPC ............ *A61N 1/44* (2013.01); *A61K 31/4188* (2013.01); *A61K 33/40* (2013.01); *A61K 41/00* (2013.01);
(Continued)

(58) Field of Classification Search
CPC ...... A61N 1/44; A61K 31/4188; A61K 33/40; A61K 41/00; H01J 37/32366; H01J 37/32449; H01J 37/32825
See application file for complete search history.

(56) References Cited

U.S. PATENT DOCUMENTS

2002/0128228 A1*  9/2002  Hwu ...................... A61P 35/00
                                                              514/183
2011/0112528 A1    5/2011  Stieber
(Continued)

OTHER PUBLICATIONS

Keidar, "Plasma for cancer treatment," Plasma Sources Sci. Technol. 24, pp. 1-20, May 20, 2015 (21 pages).
(Continued)

*Primary Examiner* — Michael J Tsai
*Assistant Examiner* — Justin L Zamory
(74) *Attorney, Agent, or Firm* — NIXON PEABODY LLP

(57) ABSTRACT

A method and system of adaptive cold atmospheric based treatment for diseased tissues, such as an area with cancerous cells, is disclosed. A gas such as helium is ionized via supplying power between and anode and a cathode to create an initial cold atmospheric plasma jet. The initial plasma jet is directed toward the area for a sufficient time, such as 10 seconds, to sensitize the cells via a reactive species. A reactive treatment, such as H2O2 or TMZ, is directed to the sensitized cells. The effectiveness of the reactive treatment is increased by the process of sensitizing the cells.

20 Claims, 11 Drawing Sheets

(51) Int. Cl.
*A61K 33/40* (2006.01)
*A61K 41/00* (2020.01)
*H01J 37/32* (2006.01)

(52) U.S. Cl.
CPC .. *H01J 37/32366* (2013.01); *H01J 37/32449* (2013.01); *H01J 37/32825* (2013.01)

(56) References Cited

U.S. PATENT DOCUMENTS

| | | | | |
|---|---|---|---|---|
| 2014/0378892 A1* | 12/2014 | Keidar | ............... | A61B 18/042 |
| | | | | 604/23 |
| 2016/0001052 A1* | 1/2016 | Zucker | ............... | A61K 33/00 |
| | | | | 604/24 |
| 2016/0030760 A1 | 2/2016 | Srb | | |

OTHER PUBLICATIONS

Yan et al., "Cold Atmospheric Plasma, a Novel Promising Anticancer Treatment Modality," Oncotarget, 8(9): 15977-15995, Nov. 11, 2016 (19 pages).

Keidar, "A prospectus on innovations in the plasma treatment of cancer," Physics of Plasmas 25, 083504, doi:10.1063/1.5034355, Aug. 8, 2018 (7 pages).

International Search Report and Written Opinion in International Application No. PCT/US2019/034999, mailed Aug. 20, 2019 (9 pages).

* cited by examiner

METHOD AND SYSTEM OF SENSITIZING CANCER CELLS TO CHEMICAL TREATMENT BY PLASMA BASED ACTIVATION

PRIORITY CLAIM

The present application claims priority to PCT Application No. PCT/US2019/034999 filed on May 31, 2019, which claims priority to U.S. Provisional Ser. No. 62/679,174, filed Jun. 1, 2018. The entireties of these applications are hereby incorporated by reference.

STATEMENT OF GOVERNMENT SUPPORT

The subject matter of this application was made with support from the United States government under a contract awarded by the National Science Foundation, Grant Number 1465061. The United States government has certain rights in the invention.

TECHNICAL FIELD

The present invention relates generally to treatments involving cold atmospheric plasma systems, and more particularly, to treating cancer cells by an adaptive cold atmospheric plasma system to be sensitive to reactive species.

BACKGROUND

Cancer is a well-known health issue. There is a large amount of research geared toward effective treatment of cancerous cells. One area of the research has been directed toward methods of eradicating cancerous cells such as chemotherapy or plasma. Plasma is an ionized gas that is typically formed in high-temperature laboratory conditions. Recent progress in atmospheric plasmas has led to cold atmospheric plasma (CAP) devices with an ion temperature close to room temperature. The unique chemical and physical properties of cold atmospheric plasma have enabled its recent utilization in various biomedical applications including cancer therapy.

Cold atmospheric plasma is an ionized near-room temperature gas, composed of reactive species, neutral particles and molecules, electrons and other physical factors such as electromagnetic field, weak ultraviolet radiation and weak heating effect. Cold atmospheric plasma has been widely used in many branches of modern medicine, including wound healing and sterilization. Over the past decade, cold atmospheric plasma has shown promising application in cancer treatment. Cold atmospheric plasma can effectively and selectively kill dozens of cancer cell lines in vitro through a direct cold atmospheric plasma treatment on the cells or through an indirect cold atmospheric plasma treatment on the medium or other biologically adaptable solutions which will be further used to affect the growth of cancer cells.

The chemical factors in cold atmospheric plasma such as reactive species have been regarded as the main anti-cancer factors during cold atmospheric plasma treatment. This conclusion is strongly supported by the observation that cold atmospheric plasma-treated medium, a solution containing most long-lived reactive species originated from cold atmospheric plasma, can cause similar strong and even selective anti-cancer effect in vitro and in vivo. The long-lived reactive species include at least $H_2O_2$, $NO_2-$, and $NO_3-$. The key role of these long-lived reactive species in the cytotoxicity of cold atmospheric plasma treatment has been extensively investigated over the past decade. Using specific scavengers such as cysteine and catalase in the medium can completely eliminate the cytotoxicity of cold atmospheric plasma treatment in many cases, which may be due to the consumption of the cold atmospheric plasma-generated ROS or RNS by these scavengers. Renewing the medium immediately after cold atmospheric plasma treatment will also completely inhibit the killing effect of cold atmospheric plasma treatment. Clearly, the cytotoxicity of cold atmospheric plasma depends on these reactive species.

The direct cold atmospheric plasma treatment differs from the indirect cold atmospheric plasma treatment in terms of the short-lived reactive species and potential other effects such as physics effects of cold atmospheric plasma treatment on cells. Comparisons between the direct and indirect cold atmospheric plasma treatment under the same experimental condition are rare in plasma medicine. In the few comparisons performed under the same experimental conditions, the direct cold atmospheric plasma treatment showed a much stronger killing effect on cancer cells compared with the treatment using the cold atmospheric plasma-treated medium. The chemical components, particularly $H_2O_2$ and $NO_2$, in the medium are the same regardless of the chosen treatment strategy, direct or indirect. Therefore, there must be some unknown factors significantly affect the cytotoxicity of the reactive species on cells. This unknown factor is sensitization (or activation) of cells prior to effect of plasma formed reactive species.

In a broad sense there is a need for a method to sensitize cancer cells before standard reactive treatments to enhance the effectiveness of these reactive treatments. There is another need to use CAP treatments to minimize potentially harmful effects on healthy cells of reactive treatments by increasing the effectiveness of smaller treatment. There is another need for a CAP system that allows a limited period sensitive cell for treatment.

SUMMARY

One disclosed example is a system for sensitization treatment of an area having cancerous cells and normal cells. The system includes a plasma device to generate a cold atmospheric plasma jet between an anode and a cathode. The generated plasma jet is directed at the area having cancerous cells and normal cells. A controller is coupled to a power supply and a gas supply to control power to the anode and cathode, and gas supply to the plasma device. The controller activates the cold atmospheric plasma jet for a sufficient time to sensitize the cells via a reactive species. A treatment device is operable to apply reactive treatment to the sensitized cells after the cells are sensitized by the cold atmospheric plasma jet.

Another example is a method of treating an area having cells. A gas is ionized via supplying electrical power between and anode and a cathode to create a cold atmospheric plasma jet. The cold atmospheric plasma jet is directed toward the area for a sufficient time to sensitize the cells via a reactive species. A reactive treatment is directed to the sensitized cells.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative

DETAILED DESCRIPTION

Figure 1:
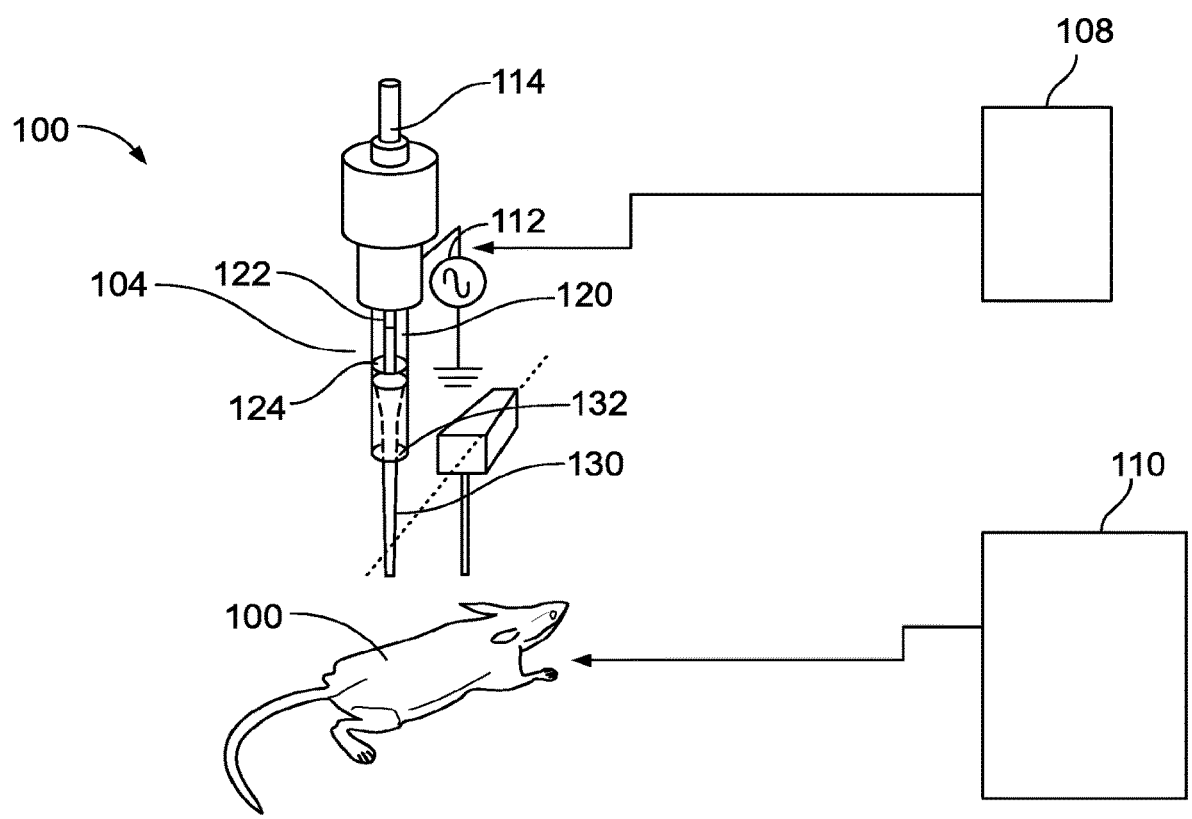
FIG. 1 is a block diagram of a CAP system for sensitizing an area of a subject with cancer cells with a plasma jet.

The present inventions can be embodied in many different forms. Representative embodiments are shown in the drawings, and will herein be described in detail. The present disclosure is an example or illustration of the principles of the present disclosure, and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed, the singular includes the plural and vice versa; and the word "including" means "including without limitation." Moreover, words of approximation, such as "about," "almost," "substantially," "approximately," and the like, can be used herein to mean "at," "near," or "nearly at," or "within 3-5% of," or "within acceptable manufacturing tolerances," or any logical combination thereof, for example.

In reference to the below examples, a novel process to sensitize cancer cells to a series of chemicals from a cold atmospheric plasma treatment in a carrier gas such as helium is disclosed. The chemicals include reactive oxygen species and reactive nitrogen species by the activation effect of the cold atmospheric plasma (CAP) treatment. Cold atmospheric plasma is a near-room temperature ionized gas composed of electrons, neutral particles, charged particles, and reactive species. The complicated composition of CAP leads to a complex interaction between the CAP and a biological system at both cellular and tissular levels.

The below disclosure relates to using a CAP treatment as an anti-cancer modality. CAP shows remarkable selective anti-cancer capacity over dozens of cancer cell lines in vitro. CAP also shows a strong anti-tumor capacity for the subcutaneous xenografted tumors or melanoma in a mouse model. The CAP treatment also generates diverse reactive species, including reactive oxygen species (ROS) and reactive nitrogen species (RNS). These reactive species have been regarded as the main anti-cancer factor in CAP treatment. The application of CAP treatment thus sensitizes cancer cells for a period of time to increase the effectiveness of conventional cancer treatment such as chemotherapy or radiation.

FIG. 1 is a block diagram of an in vivo cancer treatment system 100 that subjects an area of normal cells and cancerous cells on a subject 102 to a cold atmospheric plasma jet. In this example, the subject 102 is a test subject such as a laboratory animal, but it is to be understood the system 100 may be used as part of the treatment for patients with cancerous cells. The system 100 includes a cold atmospheric plasma emitter device 104. A controller 108 allows a user to control the intensity and duration of the cold atmospheric plasma to selectively sensitize the cancerous cells. As will be explained, the controller 108 is operative to control application of the cold atmospheric plasma jet from the emitter device 104. Thus, the controller 108 allows control of the plasma jet to increase sensitivity of cancerous cells. A treatment system 110 such as a medicine dispensary for chemotherapy or radiation device is provided for treatment of cancerous cells in the subject 102 after the application of the cold atmospheric plasma.

The cold plasma emitter device 104 includes a power supply 112, a gas source 114, and a glass tube 120. In this example, the glass tube 120 holds an anode 122, and a cathode 124. The tube 120 may also be fabricated from any suitable material such as quartz. Power to the anode 122 and the cathode 124 from the power supply 112 produces a plasma jet 130 from a nozzle 132 formed on the glass tube 120.

The high voltage power supply 112 is electrically connected to the anode 122 and cathode 124 and provides a high voltage supply to the anode 122 and cathode 124 through cables. The controller 108 is coupled to the high voltage power supply 112 and regulates the discharge voltage and frequency that is applied to the anode 122 and cathode 124 and therefore controls the intensity of a plasma jet 130 emitted by the nozzle 132. Alternatively, the controller 108 may regulate the discharge current to regulate the plasma jet 130 via the power supply 112.

The gas source 114 can be pressurized, so that gas travels through a supply tube into the inside space of the glass tube 120. A separate gas controller (not shown) may be provided to control the flow rate of the gas in the glass tube 120, or the gas controller may be integrated with the controller 108.

The gas then continues through the glass tube 120 and exits the glass tube 120 through the nozzle 132 as the jet or stream flow 130. The gas source 114 may include multiple gas sources for mixtures of different gases such as helium, argon, and nitrogen. The controller 108 or separate gas controller can also control gas composition in the example of multiple gas sources as well as the flow rate of the gasses in the composition.

As the gas enters the glass tube 120, the anode 122 and the cathode 124 excite the gas, thereby ionizing the gas to form a cold plasma jet. In this example, the gas is helium, though other gases such as nitrogen may be used. Thus, as the gas is discharged out of the nozzle 132, it is a cold plasma jet. The cold plasma jet or stream flow 130 diffuses over time. In accordance with this example, the plasma is provided at a flow rate of 10-17 liters per minute, with the voltage supply being 5 kV and at 30 kHz. At that configuration, the plasma will have a high ionization as it exits the glass tube 120. Accordingly, the glass tube 120 is preferably placed at a predetermined distance from the target cells of the subject 102 being treated.

The glass tube 120 allows the plasma to be targeted at desired cancer cells in the skin to selectively sensitize the cancerous cells in an area of the subject 102. The glass tube 120 may be utilized, for instance, to sensitize cells of any cancer type that is close to the skin and can be applied without surgery, such as for breast, colon, lung, bladder, or oral cancers. With surgery, the system 100 may be applied to any tumor. In this example, the flow rate may be 10-17 liters/min., with a voltage of 2-5 kV and a frequency of 10-50 KHz. Of course, other flow rates, voltages, currents, and frequencies may be used. For example, in the case of localized treatment, a flow rate of 0.1 liters/min. may be used. The nozzle 132 may be between 3-5 mm diameter and the distance between the anode 122 and the cathode 124 may be 5-10 mm. At the predetermined distance, the plasma will have diffused to a desirable level. However, the intensity of the plasma will continue to decrease as the target area is moved further from the glass tube 120, and the plasma will be essentially entirely dissipated at a distance of 5 cm from the glass tube 120 in this example. The plasma is well collimated the entire length up to about 5 cm from the glass tube 120. The plasma jet stream is discontinuous and represents a series of propagating plasma bundles. In this example, a mechanical actuator may be deployed to move the location of the glass tube 120 and thereby change the predetermined distance between the glass tube 120 and the target area. The mechanical actuator may be controlled by the controller 108.

Figure 2A:
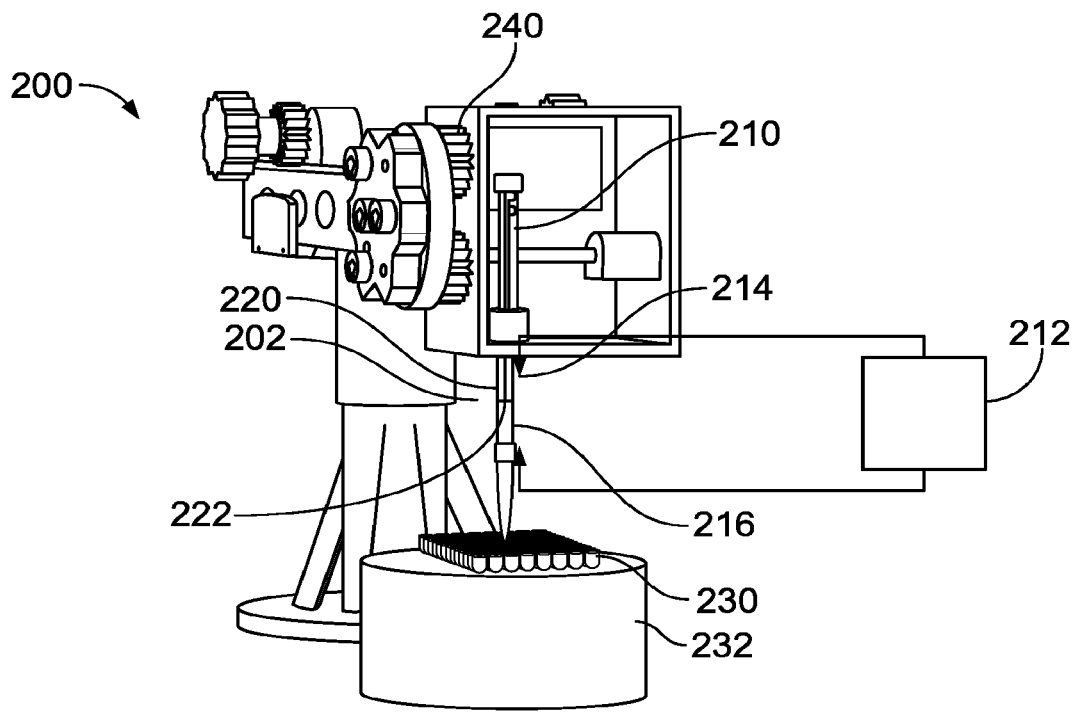
FIG. 2A is a block diagram of a CAP system for in vivo treatment of cells in a test system.

FIG. 2A shows an experimental CAP based in vitro system 200 for testing the effect of CAP to increase cancer cell sensitivity to reactive treatments. The system 200 includes a CAP jet device 202. The CAP jet device 202 includes a gas supply 210, a power source 212, a central anode 214 and a ring grounded cathode 216. A glass tube 220 carries a carrying gas from the gas supply 210.

Similar to the system 100 in FIG. 1, the glass tube 220 includes a nozzle 222 that allows the emission of the plasma jet from the application of power from the power source 212 to the anode 214 and the cathode 216. The plasma jet is directed toward a well plate 230 that is supported by a base 232. In this example, the well plate 230 includes 96 wells. Each of the wells in the well plate 230 hold test cells and a medium. A mechanical actuator 240 allows the positioning of the distance between the glass tube 220 and the well plate 230. The mechanical actuator 240 also allows the glass tube 220 and thereby the plasma jet to be positioned above individual wells in the well plate 230.

In this example, helium is used as the carrying gas to trigger the discharge process and the formation of the CAP jet. The CAP jet is formed through the discharge between the ring grounded cathode 216 and the central anode 214 and is flowed out by the helium in the glass tube 120 with a diameter of 4.5 mm. The discharge process is driven by an AC high voltage with a frequency of 12.5 kHz. In this example, the discharge voltage (peak value) between the ring grounded cathode 216 and the central anode 214 range from 3.15 kV to 4.94 kV. The discharge process is driven by a pulsed generator with a frequency between 10 kHz to 15 kHz. The flow rate ranges from 1.062 liter/min (lpm) to 4.763 lpm. The highest temperature of the CAP jet was 40° C. during all the experiments explained below. The distance between the down edge of class tube 220 and the bottom of the 96-well plate 230 is 27.5 mm. Of course, other distances, flow rates, voltages and frequencies may be used.

Figure 2B:
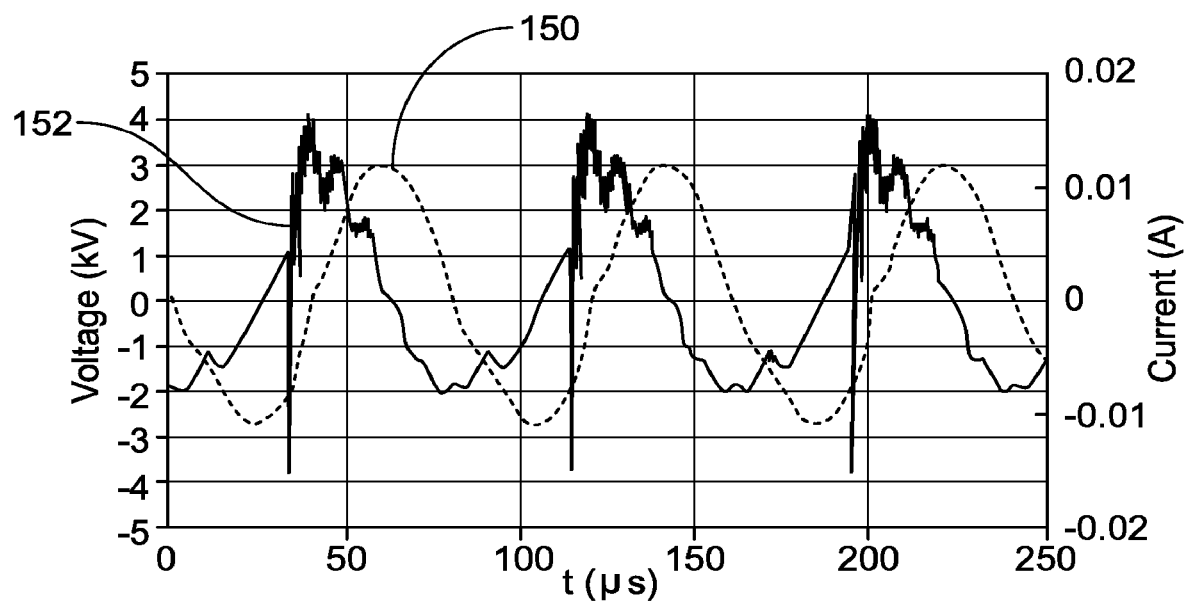
FIG. 2B is a graph of the discharge current and voltage signals for the system in FIG. 2A.
Figure 2C:
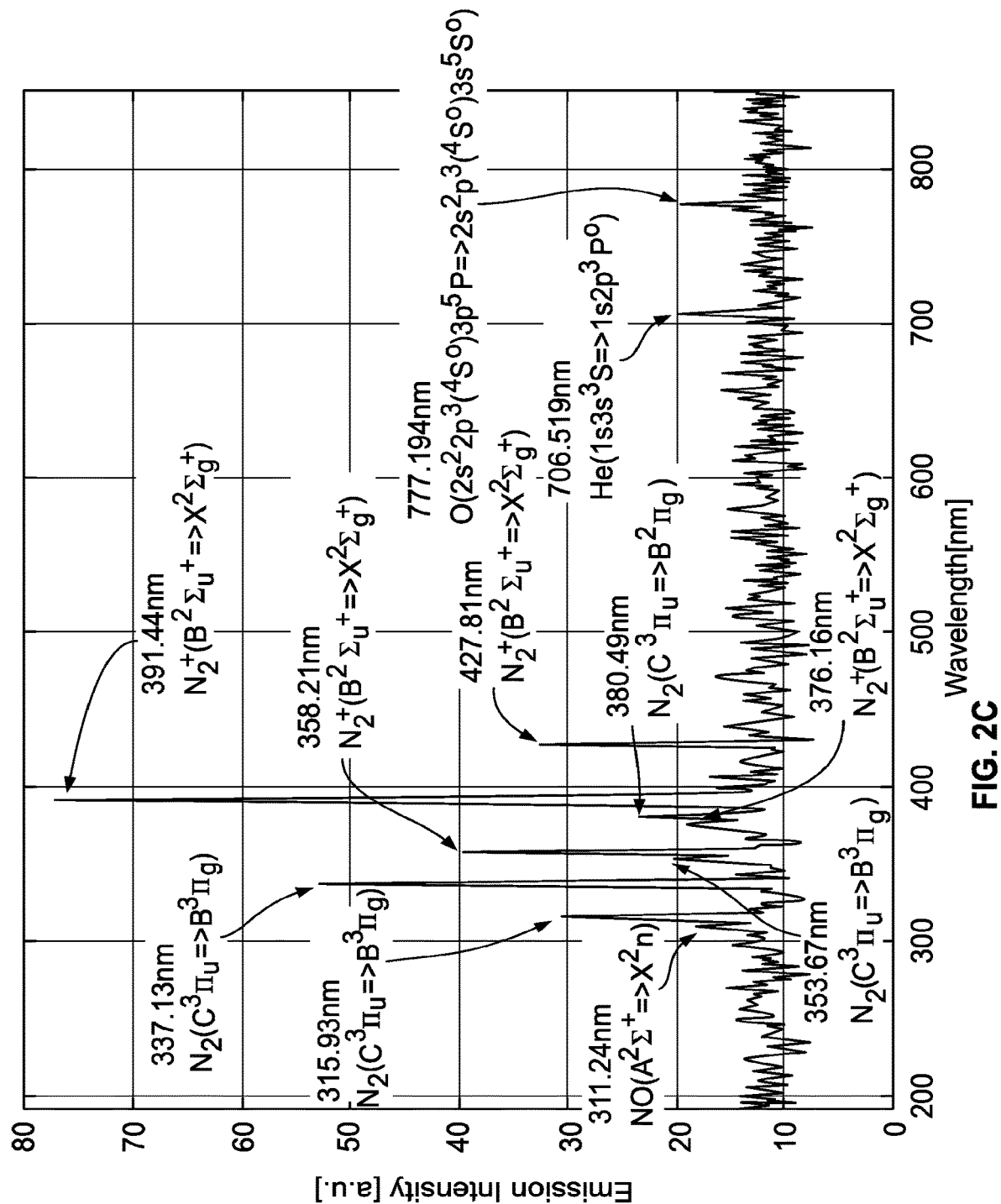
FIG. 2C is a set of optical emission spectrum images of different cold atmospheric plasma jets generated for the test system in FIG. 2A.
Figure 2D:
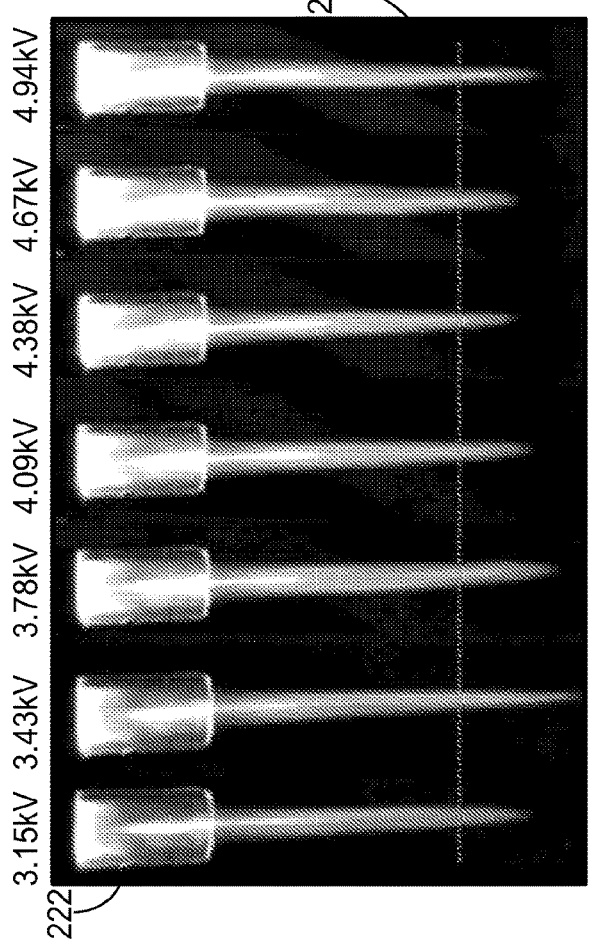
FIG. 2D is a set of optical emission spectrum images of the cold atmospheric plasma jets generated for the test system in FIG. 2A.

The discharge voltage and current were measured using an oscilloscope in this example. FIG. 2B is a graph showing a waveform for the discharge voltage 250 and a waveform for the discharge current 252. FIG. 2C is a graph showing optical emission spectrum (OES) of the CAP jet at 20 mm down to the glass nozzle 222 and 5 mm away from the jet axis. Optical images of the plasma jet are shown in FIG. 2D for different voltages ranging from 3.15 kV to 4.94 kV. The CAP treatment was performed by a vertical treatment on the cancer cells immersed in a thin layer of medium in the wells of the well plate 230. A line 270 represents the bottom of the wells of the well plate 230 holding the experimental cells and medium.

In this example, human pancreas adenocarcinoma (PA-TU-8988T) cells were used in conjunction with a Dulbecco's modified Eagle's medium (DMEM, 11965-118) from Life Technologies. The DMEM was mixed with 1% (v/v) antibiotic (penicillin and streptomycin) solution (Life Technologies). The media used in the cell culture were composed of DMEM supplemented with 10% (v/v) fetal bovine serum (ThermoFisher Scientific). The cells were cultured in a 96-well plate (61406-081, Corning). 100 μL of the cells-harvesting solution ($3\times10^4$ cells/mL) were seeded in each well. Cancer cells were grown for 1 day under the standard culture condition (a humidified, 37 C, 5% CO2 environment). The media used to culture cells overnight were removed before any experiments were performed.

In the example system 200 in FIG. 2A, basic protocols were provided to determine the activation state of cancer cells. To perform the CAP sensitivity treatment, each well of the well plate 230 was filled with a 50 μL DMEM solution with the growing cells. Each of the cells in the 96-well plate 230 was treated by the CAP jet from the CAP jet device 202 vertically. The gap between the bottom of the 96-well plate 230 and the CAP source is 3 cm in this example. After the CAP treatment, 50 μL of new DMEM was transferred to replace the medium in the wells of the 96-well plate 230 treated by the CAP jet device 202.

As a result, cancer cells in the activation state were obtained when the CAP sensitivity treatment time was longer than 20 seconds. Reactive treatment was applied in the form of new H2O2 – DMEM added to the cells in the well plate 230. To make the new H2O2 – DMEM, 9.8 M H2O2 standard solution (Sigma-Aldrich, 216763) was added to DMEM with a designed concentration. Then, H2O2 – DMEM or NO2 – DMEM was transferred to affect the activated cancer cells in the designed experiments. The cell viability was measured by using MTT assay according to the standard protocols provided by the manufacturer (Sigma-Aldrich, M2128). The 96-well plate 230 was read by an H1 microplate reader manufactured by Hybrid Technology at an absorbance of 570 nm after shaking in the reader for 30 seconds. To perform the data analysis, the measured absorbance at 570 nm was processed to be a relative cell viability by the division of absorbance between the experimental group and the control group.

One minute of the direct CAP treatment on cells from the system 200 causes a strong killing effect (about 80%) on PA-TU-8988T cells. A quick removal of the medium containing ROS and RNS after the CAP treatment will counteract the cytotoxicity of the CAP treatment. In such a case, the activation of cancer cell sensitivity still exists and will last about 5 hours. When the reactive species were removed, the cytotoxicity of the CAP sensitivity treatment is nearly completely inhibited, because the activation will not cause noticeable cytotoxicity on cancer cells.

The CAP treatment and removal of the medium containing reactive species is the basic strategy to obtain the cancer cells in the activated state. Thus, the process for increasing the effectiveness of treating cancer cells with a follow up reactive treatment is as follows. The direct CAP sensitivity treatment (1 min) was first performed on each well of the 96-well plate 230. The cancer cells in the wells were immersed in 50 µL of DMEM. The DMEM was quickly removed (less than a minute) after the CAP sensitivity treatment. Then, the CAP-activated (treated) cancer cells were obtained. The cytotoxicity of H2O2 (10 µM) treatment on the CAP-treated (activated) cancer cells were compared with that on cancer cells without the CAP sensitivity treatment. The H2O2-containing DMEM was made by adding H2O2 standard solution (Sigma-Aldrich, 216763) in DMEM with a designed concentration (10 µM). All cells were cultured for 3 days before the final cell viability assay using a MTT assay (Sigma-Aldrich, M2128). The cell viability assay was performed following the standard protocols provided by the manufacturer. Finally, the absorbance at 570 nm was processed to be a relative cell viability (fold) by the division of absorbance between the experimental group and the control group. In the control group, cancer cells were just cultured in the untreated DMEM.

Thus, the existence of an activation state on the CAP-treated cancer cells after treatment applied by the system in FIG. 1 or FIG. 2A allows for more effective following reactive treatment. These cancer cells are sensitized by diverse reactive species generated by CAP or by other methods. The CAP treatment changes the cancer cells instantly after the treatment. The CAP treatment drastically decreases the threshold of the vulnerability of cancer cells to the cytotoxicity of the CAP-originated reactive species such as H2O2. The activation state of cancer cells does not cause noticeable cytotoxicity. The CAP-treated cancer cells gradually lose sensitivity to reactive species over the initial 2 hours after the CAP treatment.

Figure 3:
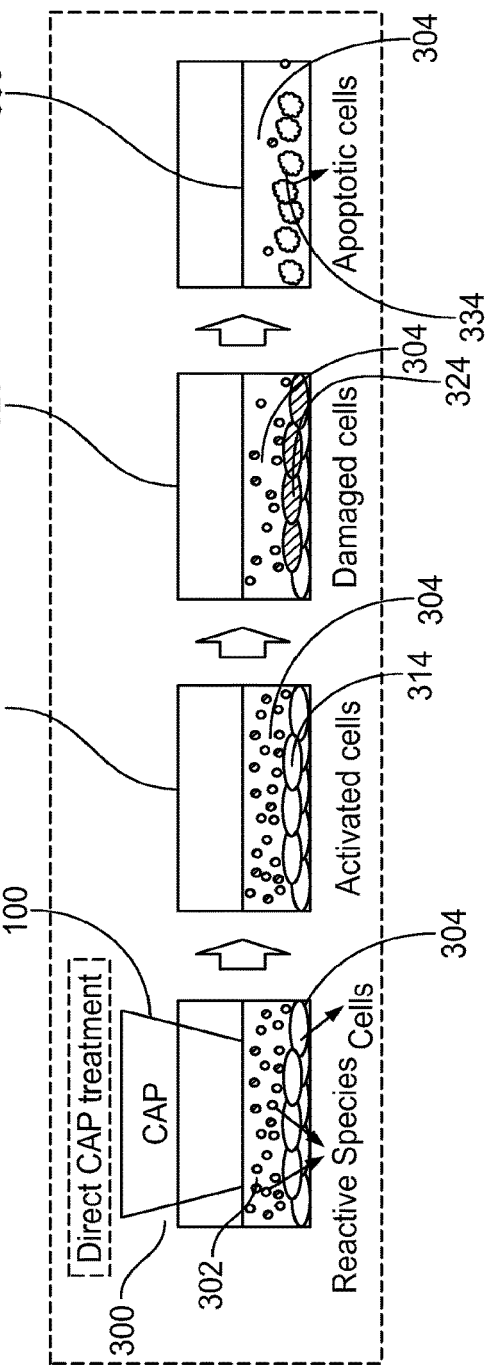
FIG. 3 is a diagram showing the different states of cancer cells after sensitivity to the CAP Treatment.

FIG. 3 shows different stages of the cancerous cells during the process involving CAP sensitivity treatment and reactive treatment. A first stage 300 occurs with the application of a CAP sensitivity treatment via a system such as the system 100 in FIG. 1. A series of reactive species 302 is created in the cancer cells 304. A second stage 310 occurs immediately post application of the CAP sensitivity treatment. In the second stage 310, the reactive species 302 are still largely present. The cancer cells are now activated cells 314 based on the treatment of the CAP system. A third stage 320 occurs after the application of a cancer treatment such as a medium with H2O2. The reactive species 302 have begun to diminish. The activated cells have now become damaged cells 324 due to the application of the reactive treatment. A fourth stage 330 occurs after the application of the reactive treatment. In the fourth stage, the reactive species 302 have largely disappeared, but the damaged cells have become apoptotic cells 334 due to the increased sensitivity that is created by the CAP to the reactive treatment.

Figure 4:
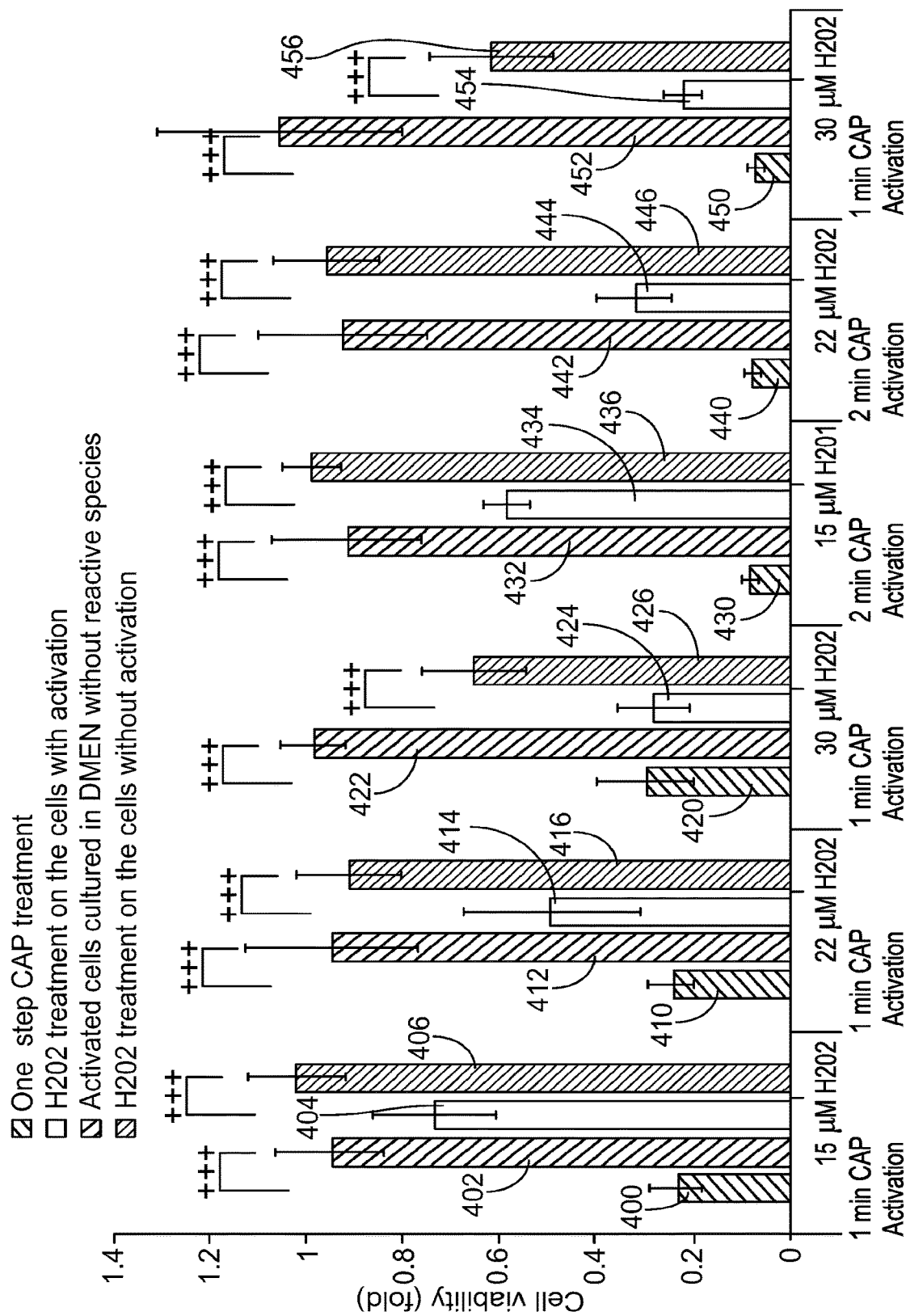
FIG. 4 is a bar graph of test results of the CAP sensitivity treatment compared with other different processes.

One example of successful application of the above process is pancreatic cancer cells. Such cells may be activated into a special state, in which these CAP-treated cells have a drastically decreased threshold to the cytotoxicity of reactive species such as H2O2. FIG. 4 shows the results of the effects of the CAP treatment on pancreatic cancer cells. A first set of bars 400, 402, 404, and 406 shows the results of viability of cells after one minute CAP activation and selective application of 15 µM H2O2. The bar 400 shows viability of cells with no subsequent H2O2 treatment. The bar 402 shows viability of cells that are cultured by immediately removing the DMEM with reactive species and replacing it with DMEM that does not have reactive species such as H2O2. The bar 404 shows viability of cells that are activated and 15 µM H2O2 is applied. The bar 406 shows viability of cells that are treated with 15 µM H2O2 without previous activation by the CAP system.

A second set of bars 410, 412, 414, and 416 shows the results of viability of cells after one minute CAP activation and selective application of 22 µM H2O2. The bar 410 shows viability of cells with no subsequent H2O2 treatment. The bar 412 shows viability of cells that are cultured by immediately removing the DMEM with reactive species and replacing it with DMEM that does not have reactive species. The bar 414 shows viability of cells that are activated and 22 µM H2O2 is applied. The bar 416 shows viability of cells that are treated with 22 µM H2O2 without activation.

A third set of bars 420, 422, 424, and 426 shows the results of viability of cells after one minute CAP activation and selective application of 30 µM H2O2. The bar 420 shows viability of cells with no subsequent H2O2 treatment. The bar 422 shows viability of cells that are cultured by immediately removing the DMEM with reactive species and replacing it with DMEM that does not have reactive species. The bar 424 shows viability of cells that are activated and 30 µM H2O2 is applied. The bar 426 shows viability of cells that are treated with 30 µM H2O2 without activation by the CAP system.

A fourth set of bars 430, 432, 434, and 436 shows the results of viability of cells after two minute CAP activation and selective application of 15 µM H2O2. The bar 430 shows viability of cells with no subsequent H2O2 treatment. The bar 432 shows viability of cells that are cultured by immediately removing the DMEM with reactive species and replacing it with DMEM that does not have reactive species. The bar 434 shows viability of cells that are activated and 15 µM H2O2 is applied. The bar 436 shows viability of cells that are treated with 15 µM H2O2 without activation by the CAP system.

A fifth set of bars 440, 442, 444, and 446 shows the results of viability of cells after one minute CAP activation and selective application of 22 µM H2O2. The bar 440 shows viability of cells with no subsequent H2O2 treatment. The bar 442 shows viability of cells that are cultured by immediately removing the DMEM with reactive species and replacing it with DMEM that does not have reactive species. The bar 444 shows viability of cells that are activated and 22 µM H2O2 is applied. The bar 446 shows viability of cells that are treated with 22 µM H2O2 without activation by the CAP system.

A sixth set of bars 450, 452, 424, and 456 shows the results of viability of cells after one minute CAP activation and selective application of 30 µM H2O2. The bar 450 shows viability of cells with no subsequent H2O2 treatment. The bar 452 shows viability of cells that are cultured by immediately removing the DMEM with reactive species and replacing it with DMEM that does not have reactive species. The bar 454 shows viability of cells that are activated and 30 µM H2O2 is applied. The bar 456 shows viability of cells that are treated with 30 µM H2O2 without activation by the CAP system.

Figure 5:
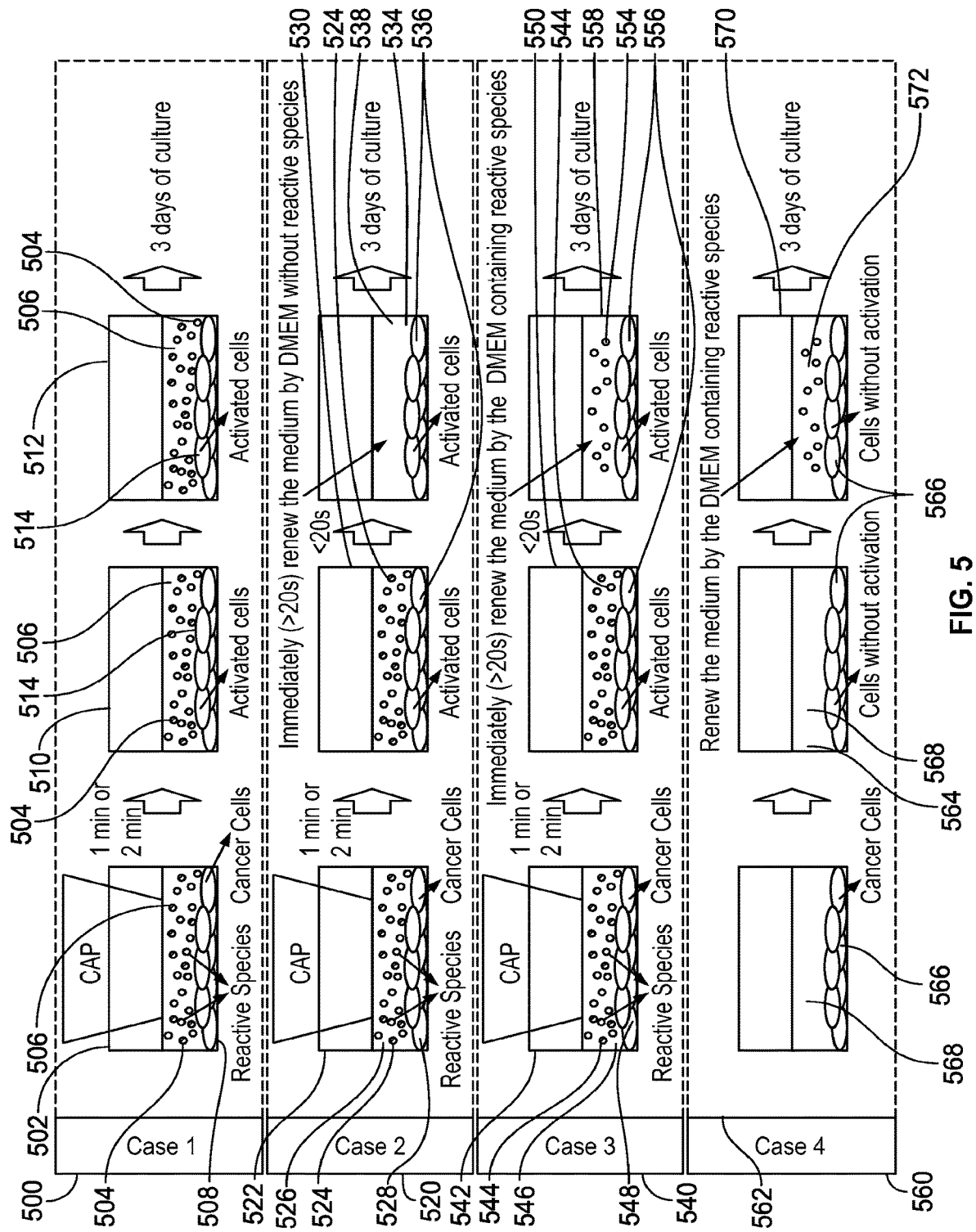
FIG. 5 shows the different processes with and without the CAP sensitivity treatment used to generate the data for the bar graph in FIG. 4.

FIG. 5 shows the different processes for preparing the cells corresponding to the results represented by the bars in FIG. 4. FIG. 5 shows a first case 500 that corresponds to bars 400, 410, 420, 430, 440, and 450 in FIG. 4. In the case 500, a first stage 502 applies the CAP treatment to create a reactive species 504 in an example DMEM 506 around cancer cells 508. Proceeding stages 510 and 512 show that the reactive species 504 remain and the cancer cells 508 are activated into activated cells 514.

FIG. 5 shows a second case 520 that corresponds to bars 402, 412, 422, 432, 442, and 452 in FIG. 4. In the case 520, a first stage 522 applies the CAP treatment to create a reactive species 524 in an example DMEM 526 around cancer cells 528. An immediately subsequent stage 530 shows that the reactive species 524 remain and the cancer cells become activated cancer cells 536. A final stage 538 shows the removal of the DMEM 526 with the reactive species and replacement with DMEM without reactive species 534 after about 20 seconds. The activated cancer cells 536 remain in the final stage 538.

FIG. 5 shows a third case 540 that corresponds to bars 404, 414, 424, 434, 444, and 454 in FIG. 4. In the case 540, a first stage 542 applies the CAP treatment to create a reactive species 544 in an example DMEM 546 around cancer cells 548. An immediately proceeding stage 550 shows that the reactive species 544 remain and the cancer cells become activated cancer cells 556. A final stage 558 shows the removal of the DMEM 546 with the reactive species 544 and replacement with DMEM with reactive H2O2 species 554 after about 20 seconds. The activated cancer cells 556 remain in the final stage 558.

FIG. 5 shows a fourth case 560 that corresponds to bars 406, 416, 426, 436, 446, and 456 in FIG. 4. In the case 560, a first stage 562 and a second stage 564 both include cancer cells 566 in an example DMEM 568. No activation is performed. A final stage 570 shows the removal of the DMEM 568 and replacement with a DMEM solution with reactive H2O2 species 572 after about 20 seconds. The cancer cells 566 remain unactivated in the final stage 570.

The treatments with activation as shown in bars 400, 410, 420, 430, 440, and 450 result in the most effectiveness in reducing cancer cell viability. The results shown in FIG. 4 show that CAP treatment will activate pancreatic adenocarcinoma cells (PA-TU-8988T) into a sensitive state, in which the cancer cells can be much more easily killed by reactive species, such as H2O2 as shown in bars 404, 414, 424, 434, 444, and 454, as compared with the cancer cells without such activation as shown in bars 406, 416, 426, 436, 446, and 456. Thus, FIG. 4 shows the chemical effect of ROS has been drastically magnified through the activation state of cancer cells. For example, 22 µM H2O2 – DMEM (bars 414 and 444) can strongly kill the cancer cells activated by CAP treatment, though 22 µM H2O2 – DMEM will only cause a very small inhibition on the cell viability of the cancer cells without the CAP treatment (bars 416 and 446). Thus, a direct CAP treatment causes much stronger cytotoxicity over cancer cells compared with an indirect CAP treatment.

Specifically, when H2O2 is used to treat the CAP-treated cancer cells, the strong sensitivity of these cells to the cytotoxicity of H2O2 was demonstrated. The H2O2 – DMEM (15 µM and 22 µM) did not cause strong killing effect on PA-TU-8988T cells without an activation as shown in bars 406, 416, 436 and 446. In contrast, the same H2O2 treatment on the CAP-activated PA-TU-8988T cells will cause a strong killing effect as shown by bars 404, 414, 434, and 444. For example, the killing effect of 22 µM H2O2 on the cancer cells activated by CAP and the cancer cells without activation was about 10% as shown by bars 416 and 446 and 50% as shown by bars 414 and 444, respectively. A similar trend was observed on other H2O2 treatments in FIG. 4.

Figure 6:
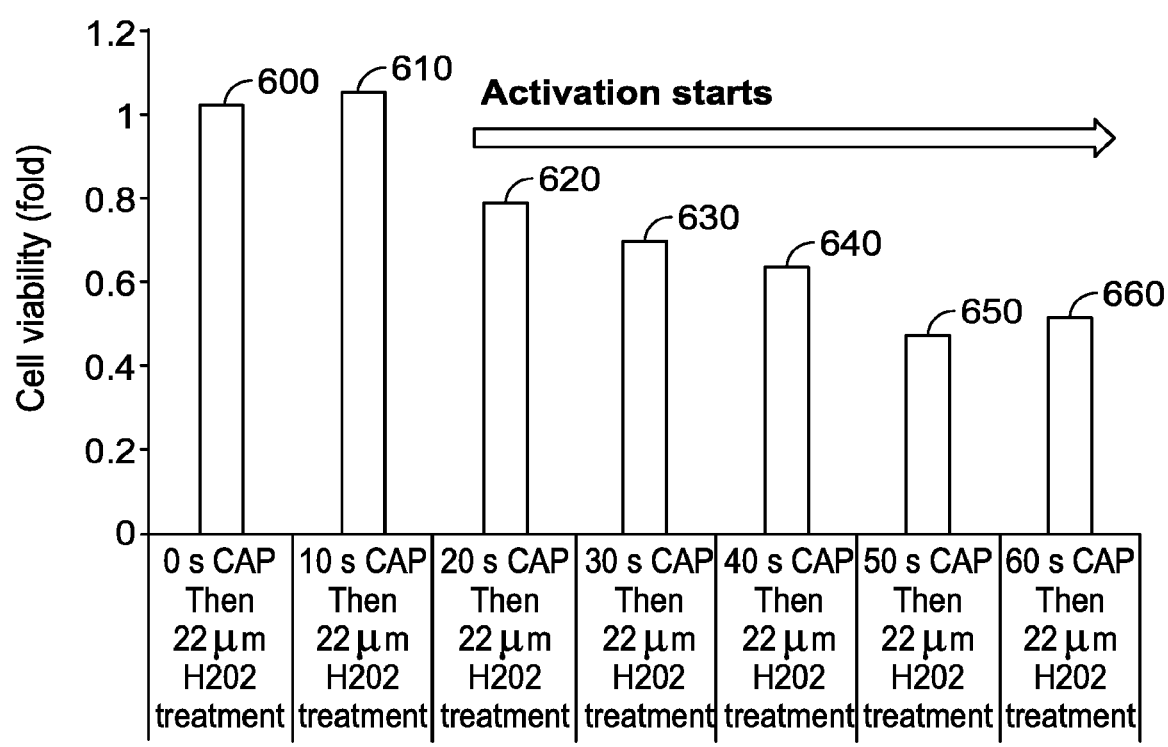
FIG. 6 is a graph showing cell viability after different times for the CAP sensitivity treatment followed by H2O2 treatment.

FIG. 6 is a graph showing cell viability after different times for CAP treatment followed by H2O2 treatment. A first bar 600 shows the viability of cells with no CAP treatment. A second bar 610 shows the viability of cells with 10 seconds of CAP treatment. A third bar 620 shows the viability of cells with 20 seconds of CAP treatment. A fourth bar 630 shows the viability of cells with 30 seconds of CAP treatment. A fifth bar 640 shows the viability of cells with 40 seconds of CAP treatment. A sixth bar 650 shows the viability of cells with 50 seconds of CAP treatment. A second bar 660 shows the viability of cells with 60 seconds of CAP treatment. The bars 620, 630, 640 and 650 show the time sequence of the activation of cancer cells the activation of cancer cells begins just 20 seconds after the CAP treatment. The activation state of the cells is proportional to the length of CAP treatment. The activation state of the cancer cells will last about 2 hours after the CAP treatment.

Figure 7A:
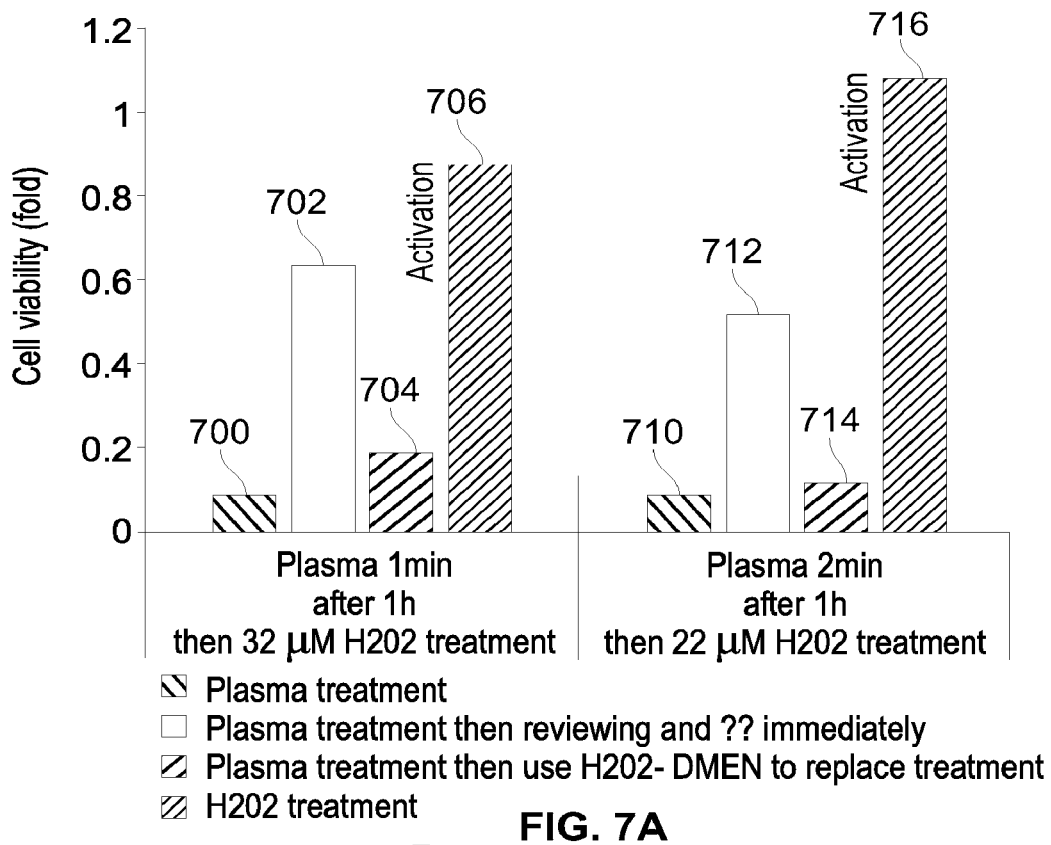
FIG. 7A is a graph showing cell viability after different times for CAP sensitivity treatment followed by H2O2 treatment and cell activation.

FIG. 7A is graph that shows the effectiveness of treatment using H2O2 one hour after the CAP treatment. FIG. 7A shows the viability of cells under different conditions one hour after the CAP treatment. A first set of bars 700, 702, 704, and 706 shows the viability of cells with a one minute CAP treatment. The bar 700 shows the results of CAP treatment alone, the bar 702 shows the results of CAP treatment then renewing the medium immediately, the bar 704 shows the results of CAP treatment and replacing the medium with H2O2 DMEM after one hour, and the bar 706 shows results of H2O2 treatment alone. A second set of bars 710, 712, 714, and 716 show the viability of cells with a two minute CAP treatment. The bar 710 shows the results of CAP treatment alone, the bar 712 shows the results of CAP treatment and then replacing the medium immediately, the bar 714 shows the results after one hour of the CAP treatment and replacing the medium with H2O2 DMEM immediately, and the bar 716 shows results of just the H2O2 treatment alone.

Figure 7B:
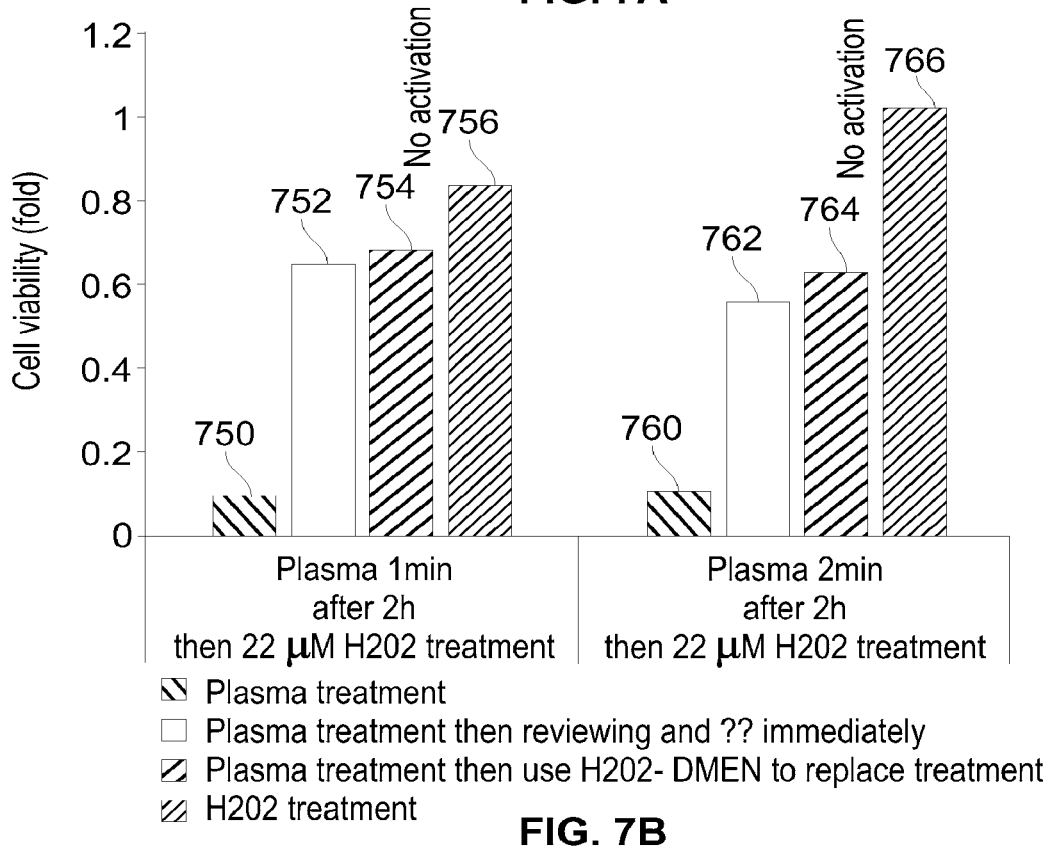
FIG. 7B is a graph showing cell viability after different times for the CAP sensitivity treatment followed by H2O2 treatment two hours later without cell activation.

FIG. 7B shows the viability of cells under different conditions two hours after the CAP treatment where no activation occurs in the cells. A first set of bars 750, 752, 754, and 756 show the viability of cells with a one minute CAP treatment. The bar 750 shows the results of CAP treatment alone, the bar 752 shows the results of CAP treatment then replacing the medium immediately, the bar 754 shows the results after one hour of CAP treatment and replacing the medium with H2O2 DMEM immediately, and the bar 756 shows results of just the H2O2 treatment alone. A second set of bars 760, 762, 764, and 766 show the viability of cells with a two minute CAP treatment. The bar 760 shows the results of CAP treatment alone, the bar 762 shows the results of CAP treatment then replacing the medium immediately, the bar 764 shows the results after an hour of CAP treatment and replacing the medium with H2O2 DMEM immediately, and the bar 766 shows results of just H2O2 treatment alone. As may be seen in comparison of bars 704 and 714 with bars 754 and 764, the cell activation effects disappear after two hours and the treatment does not have any effect on cell viability.

Figure 8:
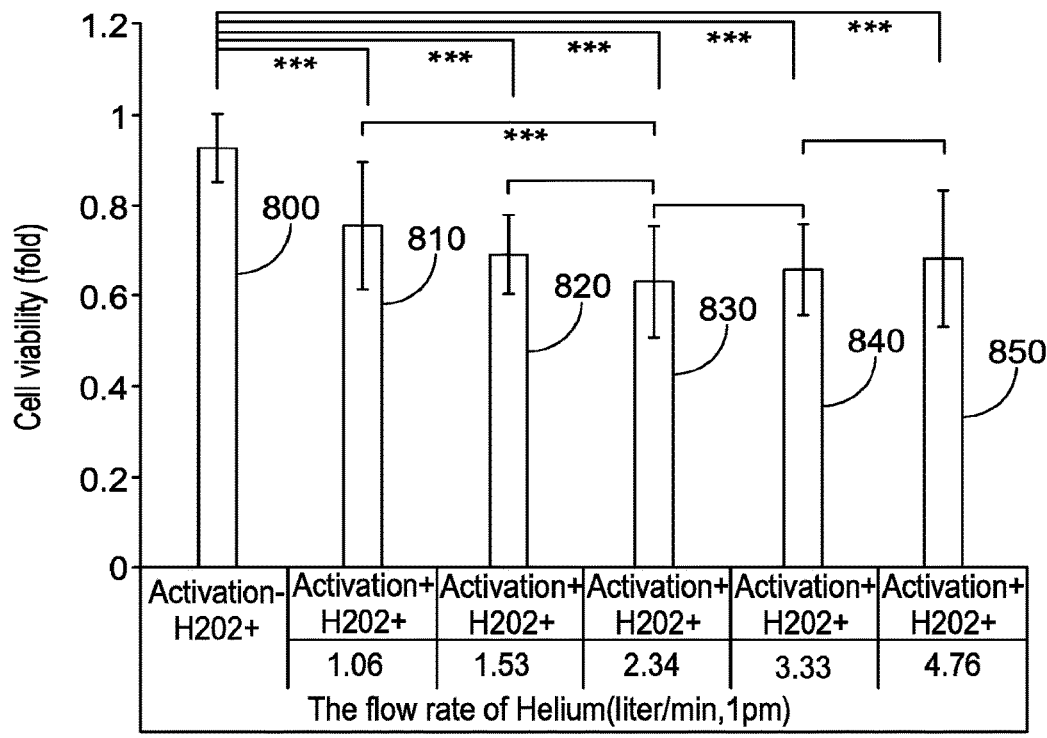
FIG. 8 is a graph of cell viability demonstrating the effect of the flow rate of helium on the activation time of the cells.

Another factor is the flow rate of helium from the test system 200 in FIG. 2 on the activation time for the cells. In one example, the flow rate of helium ranged from 1.06 lpm to 4.76 lpm. The resulting data is shown in FIG. 8. FIG. 8 shows that 10 μM H2O2 treatment will not cause a killing effect on PA-TU-8988T cells without CAP treatment (activation). However, a 10 μM H2O2 treatment will have significant killing effect on the CAP-activated PA-TU-8988T cells. This is a typical feature of the activation phenomenon. In this example, one minute of CAP treatment was performed when the discharge voltage was 3.43 kV. Activation + represents activation and activation − represents no activation of the cells in FIG. 8. Thus, a bar 800 represents the cell viability without activation. A bar 810 represents the cell viability at a flow rate of 1.06 lpm, a bar 820 represents the cell viability at a flow rate of 1.53 lpm, a bar 830 represents the cell viability at a flow rate of 2.34 lpm, a bar 840 represents the cell viability at a flow rate of 3.33 lpm, and a bar 850 represents the cell viability at a flow rate of 4.76 lpm. The H2O2 treatment (10 μM) is represented as H2O2+ under the bars 800-850. As shown in FIG. 8, the activation of PA-TU-8988T cells will be enhanced when the flow rate increases from 1.06 lpm to 1.53 lpm. The activation does not change when the flow rate increases from 1.53 lpm to 4.76 lpm. Thus, controlling the flow rate is an effective method to enhance the activation effect on the CAP-treated PA-TU-8988T cells.

Figure 9:
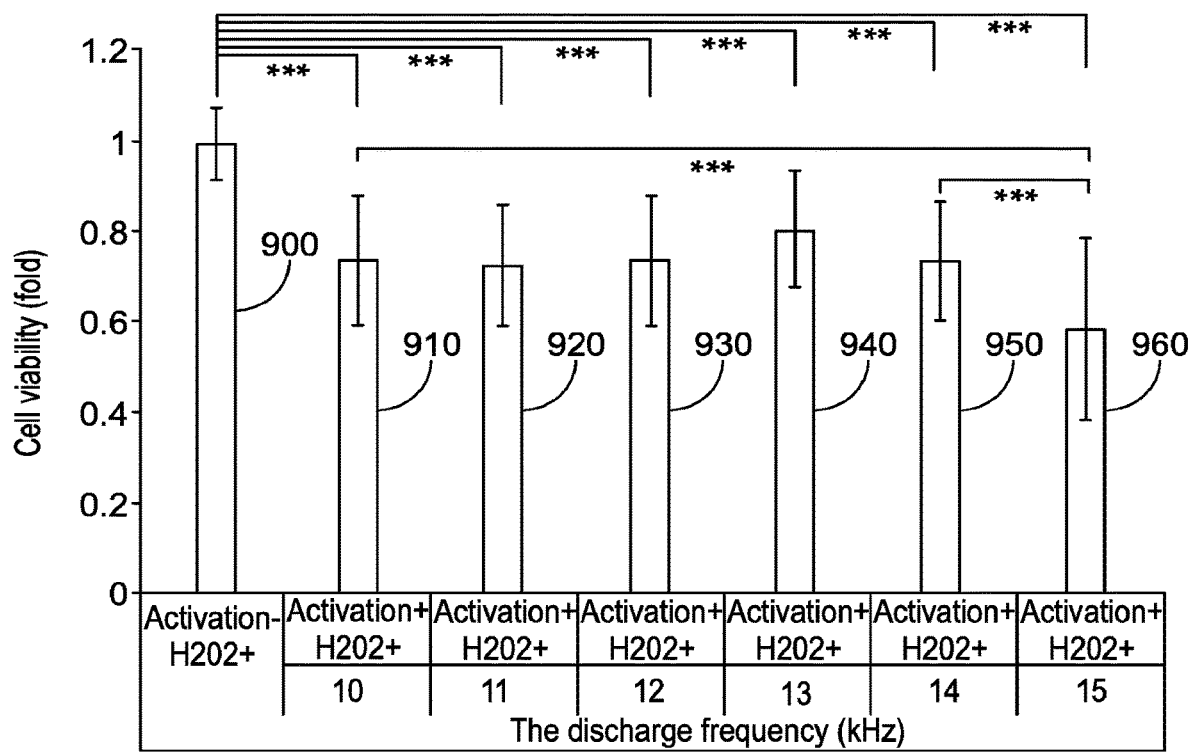
FIG. 9 is a graph of cell viability under different discharge frequencies in the CAP sensitivity treatment.

Another factor is the effect of the discharge frequency on the activation. In this example, the discharge frequency was changed from 10 kHz to 15 kHz. FIG. 9 shows the test results of varying the discharge frequency. The data in FIG. 9 was gathered with the discharge voltage and the flow rate at 3.43 kV and 1.53 lpm, respectively. Activation + represents activation and activation − represents no activation of the cells in FIG. 9. The H2O2 treatment (10 μM) is represented as H2O2 + under the bars 910-950. In FIG. 9, a bar 900 represents the cell viability without activation. A bar 910 represents the cell viability at a discharge frequency of 10 KHz, a bar 920 represents the cell viability at a discharge frequency of 11 KHz, a bar 930 represents the cell viability at a discharge frequency of 12 KHz, a bar 940 represents the cell viability at a discharge frequency of 13 KHz, a bar 950 represents the cell viability at a discharge frequency of 14 KHz, and a bar 960 represents the cell viability at a discharge frequency of 15 KHz. FIG. 9 shows that the example 10 μM H2O2 treatment will have significant killing effect on all the CAP-activated PA-TU-8988T cells and the activation phenomenon can be observed in all cases during the change of the discharge voltage. It is found that the activation on PA-TU-8988T cells will not be enhanced until the discharge frequency reaches a relative high level of 15 kHz. To achieve a strong activation effect, a higher discharge frequency is desirable within the considered range.

Figure 10:
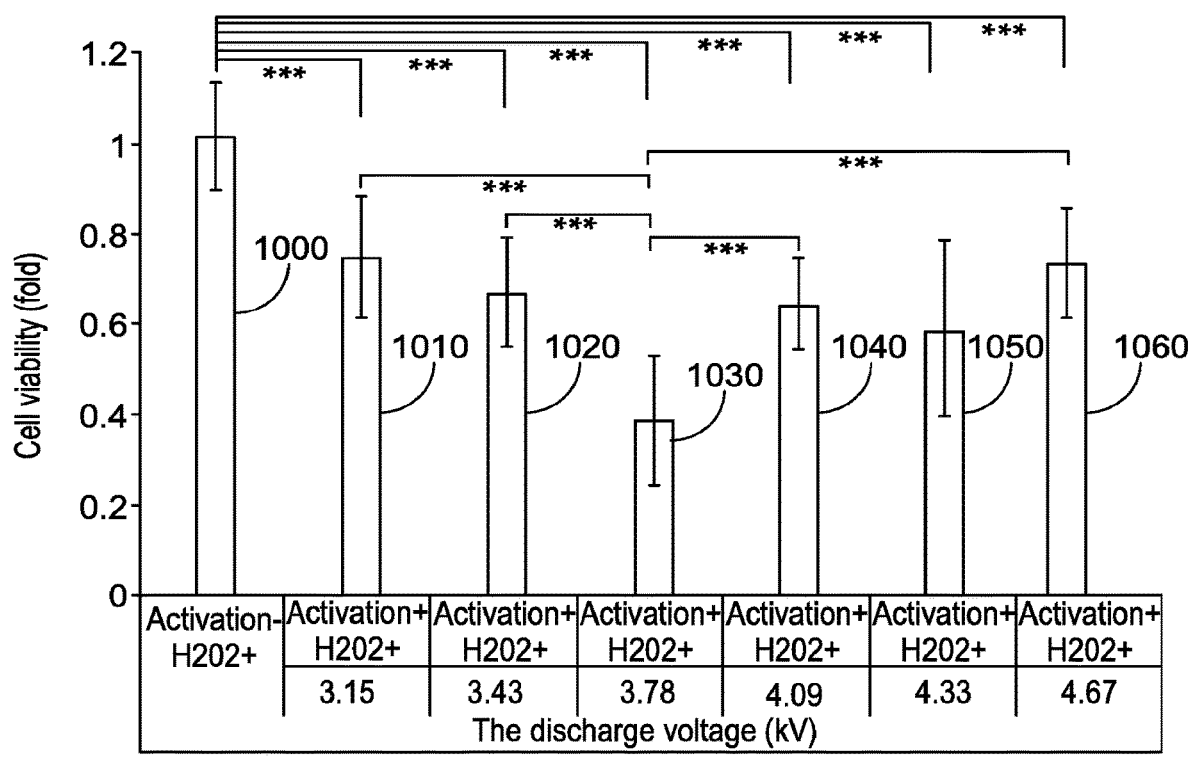
FIG. 10 is a graph of cell viability under different discharge voltages in the CAP sensitivity treatment.

Another factor is the effect of the discharge voltage. The discharge voltage between the cathode 214 and the anode 212 was tested from 3.15 kV to 4.67 kV (peak value). The activation effect on the all cases still exists. The 10 μM H2O2 treatment does not cause a killing effect on PA-TU-8988T cells without the CAP activation but results in significant killing effect on the CAP-activated PA-TU-8988T cells. FIG. 10 shows the test results of variation of the discharge voltage. In FIG. 10, a bar 1000 represents the cell viability without activation. A bar 1010 represents the cell viability at a discharge voltage of 3.15 kV, a bar 1020 represents the cell viability at a discharge voltage of 3.43 kV, a bar 1030 represents the cell viability at a discharge voltage of 3.78 kV, a bar 1040 represents the cell viability at a discharge voltage of 4.09 kV, a bar 1050 represents the cell viability at a discharge voltage of 4.38 kV, and a bar 1060 represents the cell viability at a discharge voltage of 4.67 kV. Activation + represents activation and activation − represents no activation of the cells in FIG. 10. The H2O2 treatment (10 μM) is represented as H2O2 + respectively under the bars 1000-1050. The CAP treatment was performed when the discharge frequency and the flow rate were set as 12.5 kHz and 1.53 lpm, respectively.

The maximum activation phenomenon occurs when the discharge voltage is at the middle of the discharge voltage range, i.e. 3.78 kV. The activation effect corresponding to other discharge voltages is noticeably weaker than the maximum case. For example, the cell viability decreases from 0.73 to just 0.38 when the discharge voltage increases from 3.15 kV to 3.78 kV. However, the cell viability increases again from 0.38 to 0.71 when the discharge voltage increases from 3.78 kV to 4.67 kV. Compared with other two operational parameters, a discharge voltage at the 3.78 kV shows the strongest activation effect on the CAP-treated PA-TU-8988T cells.

Another translational example application of the above described CAP treatment to sensitize cancer cells is treatment of Glioblastoma Multiforme (GBM). The most common and aggressive form of brain tumor is GBM. The current treatment plan includes surgery, chemotherapy, and radiation which is a common line of treatment for any GBM patients. Surgery and chemotherapeutics like Rapamycin, Temozolomide (TMZ), etc. offer some hope to kill the cancer cells but due to the challenging issue of crossing the blood-brain barrier (BBB), it becomes complex to deliver these drugs to the brain. Temozolomide (TMZ), an oral alkylating agent and a prodrug of the anti-cancer drug Temodar, is the standard first-line treatment for glioblastoma.

Through an in vitro study the efficacy of the non-thermal plasma technology in combination with the TMZ treatment in a chemotherapy resistant cell line (U87MG) was demonstrated. TMZ concentrations of 10 and 50 uM were tested with at least one concentration in the range found in CSF (i.e. 10-25 uM. The cell response was monitored with the Cell Titer Glo 2.0. luminescent assay (Promega). The assay determines the number of viable cells in culture by quantifying the amount of ATP present as indicated by a luminescent signal.

Figure 11A:
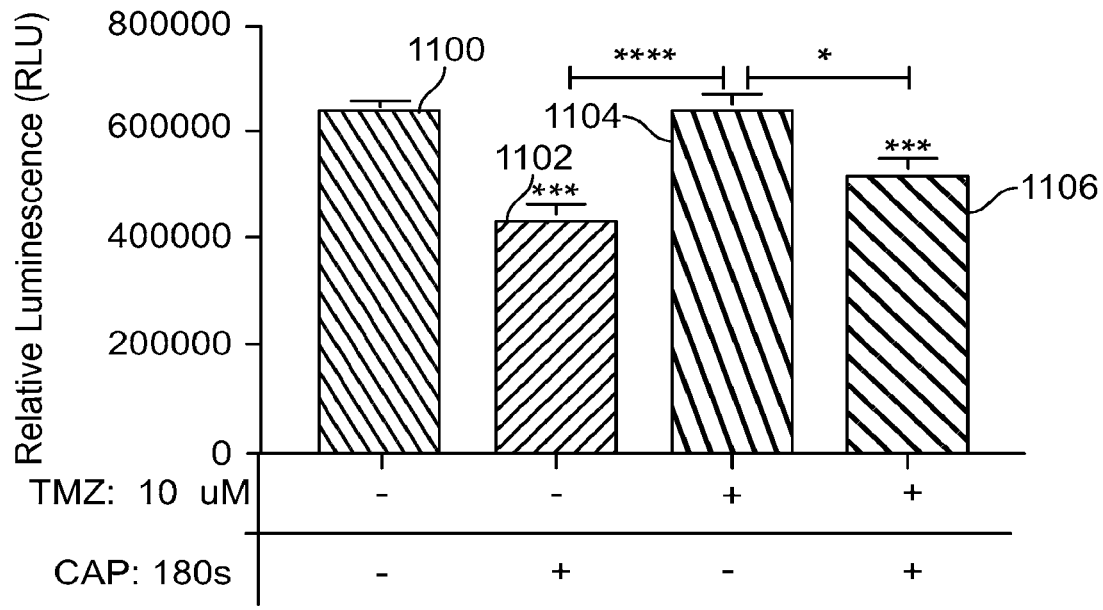
FIG. 11A is a graph of cell viability measured in terms of relative luminescence in response to plasma treatment for three minutes and temozolomide (TMZ) drug treatments.

The data underlines the successful application of plasma as a standalone therapy, while also revealing its pivotal role in successfully increasing TMZ sensitivity and reducing cell viability. FIG. 11A is a graph of cell viability measured in terms of relative luminescence in response to plasma treatment for three minutes and temozolomide (TMZ) drug treatments of 10 uM A bar 1100 represents a control group with no TMZ application or CAP treatment, a bar 1102 represents CAP treatment alone, a bar 1104 represents TMZ treatment alone, and a bar 1106 represents the CAP treatment followed by the TMZ treatment.

Figure 11B:
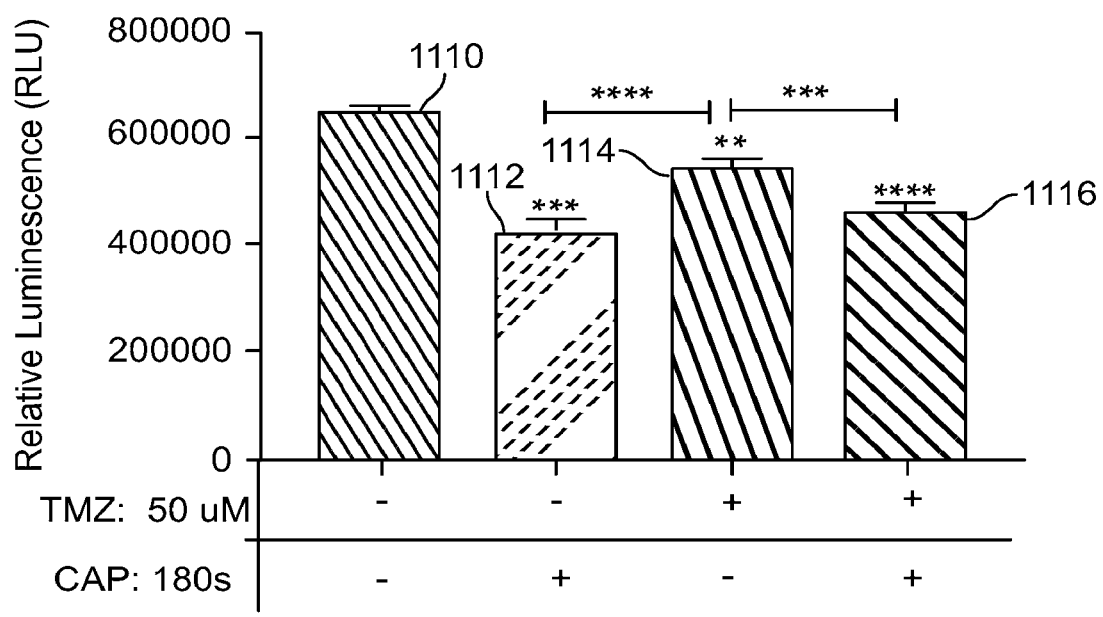
FIG. 11B is a graph of cell viability measured in terms of relative luminescence in response to plasma treatment for three minutes and temozolomide (TMZ) drug treatments.

FIG. 11B is a graph of cell viability measured in terms of relative luminescence in response to plasma treatment for three minutes and temozolomide (TMZ) drug treatments of 50 uM. As revealed by FIGS. 11A and 11B, plasma has the ability to sensitize cells to an ineffective drug concentration (10 uM) while enhancing cell death in an already effective concentration (50 uM). A bar 1110 represents a control group with no TMZ application or CAP treatment, a bar 1112 represents CAP treatment alone, a bar 1114 represents TMZ treatment alone, and a bar 1116 represents the CAP treatment followed by the TMZ treatment. As may be seen in FIGS. 11A-11B, the CAP treatment enhances the effectiveness of the TMZ treatment.

The above process involves a CAP treatment followed by a reactive treatment that is a novel tool to sensitize the cancer cells into an activation state, in which cancer cells will be sensitive to varieties of reactive species. Such an activation state will start as fast as the initial 10 seconds after the CAP treatment. The activation state will last about 2 hours before these activated cancer cells return to their initial state.

Such an activated state is the unique response of cells to CAP treatment. The activation state of cells will not cause an observable inhibition on the cell growth. It simply activates the CAP-treated cells into a unique state, in which cancer cells are very sensitive to the CAP-originated reactive species. Even a low concentration of $H_2O_2$, or $NO_2-$ can cause a noticeable killing effect on the CAP-activated cancer cells, though these reactive species will not cause significant killing effect on the same cancer cells without such activation.

The activation function of CAP treatment on pancreatic adenocarcinoma cell (PA-TU-8988T) has wide application in the cancer treatment. Many anti-cancer drugs are based on the rise of intracellular ROS. The CAP treatment may significantly enhance the anti-cancer effect of these drugs by the activation mechanism, which may be effective in treating certain chemotherapy-resistant cancer cell lines. Further, the use of activation to increase sensitivity in cells may result in a reduction of the reactive species in the reactive treatment to further protect non-cancerous cells. Thus, the treatment device 110 may be adjusted to reduce the amount or duration of the reactive treatment, such as chemotherapy or radiation, below a baseline level to account for the effect of the sensitized cancerous cells on increasing reactive treatment effectiveness.

Unless otherwise defined, all terms (including technical and scientific terms) used herein have the same meaning as commonly understood by one of ordinary skill in the art. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

While various embodiments of the present invention have been described above, it should be understood that they have been presented by way of example only, and not limitation. Numerous changes to the disclosed embodiments can be made in accordance with the disclosure herein, without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

What is claimed is:

1. A system for sensitization treatment of an area having cancerous cells and normal cells, comprising:
    a plasma device to generate a cold atmospheric plasma jet between an anode and a cathode, the generated plasma jet directed at the area having cancerous cells and normal cells;
    a controller coupled to a power supply and a gas supply to control power to the anode and cathode, and gas supply to the plasma device, the controller activating the cold atmospheric plasma jet for a sufficient time to sensitize the cells via a reactive species, the controller deactivating the cold atmospheric jet after the sufficient time; and
    a treatment device distinct from the plasma device operable to apply a reactive treatment to the sensitized cells in addition to the reactive species generated from the plasma jet after the cells are sensitized by the cold atmospheric plasma jet and the cold atmospheric plasma jet is deactivated.

2. The system of claim 1, wherein the sensitized cells are the cancerous cells.

3. The system of claim 2, wherein the cancerous cells are one of brain cancer cells, breast cancer cells, pancreatic cancer cells, skin cancer cells, bladder cancer cells, colon cancer cells, or lung cancer cells.

4. The system of claim 1, wherein the reactive treatment includes one of a solution of $H_2O_2$, or radiation.

5. The system of claim 1, wherein the controller is operative to change gas flow or gas composition generating the plasma jet.

6. The system of claim 1, wherein the controller is operative to change discharge voltage or discharge frequency generating the plasma jet.

7. The system of claim 1, wherein the gas supply supplies helium to the plasma device at a flow rate between 10-17 liters per minute.

8. The system of claim 1, wherein the discharge voltage of the plasma jet is between 2 and 5 kV and the discharge frequency of the plasma jet is between 10-50 KHz.

9. The system of claim 1, wherein the sufficient time is greater than 10 seconds.

10. The system of claim 1, wherein the reactive treatment is chemotherapy, and wherein the treatment device is operable to be adjusted to reduce the reactive treatment below a baseline level in response to the sensitized cells.

11. A method of treating an area having cells, the method comprising:
    ionizing a gas via supplying electrical power between an anode and a cathode to create a cold atmospheric plasma jet from a plasma jet device;
    directing the cold atmospheric plasma jet toward the area for a sufficient time to sensitize the cells via a reactive species;
    deactivating the cold atmospheric plasma jet after the sufficient time; and
    directing a reactive treatment, in addition to the reactive species generated from the plasma jet, to the sensitized cells from a treatment device distinct from the plasma jet device after the cold atmospheric plasma jet is deactivated.

12. The method of claim 11, wherein the selected cells are cancerous cells.

13. The method of claim 11, wherein the cancerous cells are one of brain cancer cells, breast cancer cells, pancreatic cancer cells, skin cancer cells, bladder cancer cells, colon cancer cells, or lung cancer cells.

14. The method of claim 11, wherein the reactive treatment includes one of a solution of H2O2, or radiation.

15. The method of claim 11, wherein the gas is helium, and the helium is supplied at a flow rate between 10-17 liters per minute.

16. The method of claim 11, wherein the discharge voltage of the plasma jet is between 2 and 5 kV and the discharge frequency of the plasma jet is between 10-50 KHz.

17. The method of claim 11, wherein the sufficient time is greater than 10 seconds.

18. The method of claim 11, further comprising reducing the reactive treatment below a baseline level to account for the sensitized cells.

19. The method of claim 1, wherein the reactive treatment is Temozolomide (TMZ).

20. The method of claim 14, wherein the reactive treatment is Temozolomide (TMZ).

\* \* \* \* \*